(12) United States Patent
Larsen et al.

(10) Patent No.: US 9,822,455 B2
(45) Date of Patent: Nov. 21, 2017

(54) METHOD FOR CHEMICAL ETCHING OF A NEEDLE CANNULA

(75) Inventors: Andre Larsen, Dragoer (DK); Lasse Wengel Christoffersen, Frederikssund (DK); Mikael Andersen, Malmo (DK); Jan Harald Preuthun, Broenshoej (DK)

(73) Assignee: Novo Nordisk A/S, Bagsvaerd (DK)

( * ) Notice: Subject to any disclaimer, the term of this patent is extended or adjusted under 35 U.S.C. 154(b) by 112 days.

(21) Appl. No.: 13/497,472

(22) PCT Filed: Sep. 20, 2010

(86) PCT No.: PCT/EP2010/063787
§ 371 (c)(1),
(2), (4) Date: Jul. 2, 2012

(87) PCT Pub. No.: WO2011/033102
PCT Pub. Date: Mar. 24, 2011

(65) Prior Publication Data
US 2012/0271249 A1    Oct. 25, 2012

Related U.S. Application Data

(60) Provisional application No. 61/245,435, filed on Sep. 24, 2009.

(30) Foreign Application Priority Data

Sep. 21, 2009   (EP) .................................... 09170828
Dec. 15, 2009   (EP) .................................... 09179188
Mar. 12, 2010   (EP) .................................... 10156387

(51) Int. Cl.
*B44C 1/22*    (2006.01)
*C23F 1/04*    (2006.01)
(Continued)

(52) U.S. Cl.
CPC ................. *C23F 1/04* (2013.01); *A61M 5/32* (2013.01); *B21G 1/006* (2013.01); *B21G 1/08* (2013.01);
(Continued)

(58) Field of Classification Search
CPC ...... C23F 1/02; C23F 1/04; C23F 1/14; C23F 1/16; C23F 1/28; B21G 1/006; B21G 1/08
(Continued)

(56) References Cited

U.S. PATENT DOCUMENTS 3,010,197 A     11/1961  Kanty
3,192,084 A *    6/1965  Vaughen et al. ............... 216/106
(Continued)

FOREIGN PATENT DOCUMENTS

CN          1456400 A      11/2003
DE    20 2006 003981 U1     5/2006
(Continued)

OTHER PUBLICATIONS

Kurobe, Toshiji, High Speed Slurry Flow Finishing of Inner Wall of Stainless Steel Capillary, Int'l J. of the Japan Society for Precision Engineering, vol. 32(1), Mar. 1998.
(Continued)

*Primary Examiner* — Lan Vinh
(74) *Attorney, Agent, or Firm* — Wesley Nicolas

(57) ABSTRACT

A regular metallic, cylindrical tubular needle cannula (1) is subjected to a metal etching liquid (21) in the inside lumen (4) thereby increasing the inside diameter and enhancing the flow properties while maintaining the outside appearance. The inside diameter is only increased over a controlled length (7) of the full length of the needle cannula (1) leaving sufficient length and wall thickness to also taper the outside diameter.

10 Claims, 3 Drawing Sheets

(51) Int. Cl.
*A61M 5/32* (2006.01)
*B21G 1/00* (2006.01)
*B21G 1/08* (2006.01)
*C23F 1/28* (2006.01)
*A61B 17/20* (2006.01)
*A61B 17/00* (2006.01)

(52) U.S. Cl.
CPC .............. *C23F 1/28* (2013.01); *A61B 17/205* (2013.01); *A61B 2017/00526* (2013.01); *A61M 2207/00* (2013.01)

(58) Field of Classification Search
USPC .............. 216/2, 8, 11, 83, 92, 100, 102, 103
See application file for complete search history.

(56) References Cited

U.S. PATENT DOCUMENTS

| | | |
|---|---|---|
| 3,326,785 A | 6/1967 | Williams |
| 3,326,786 A | 6/1967 | Sato |
| 4,335,718 A * | 6/1982 | Calabrese .............. A61M 5/158 604/272 |
| 4,863,555 A | 9/1989 | John, Jr. et al. |
| 5,951,528 A | 9/1999 | Parkin |
| 6,516,815 B1 | 2/2003 | Stevens et al. |
| 6,748,786 B2 | 6/2004 | Ooyauchi et al. |
| 6,988,892 B2 * | 1/2006 | Dragan et al. .................. 433/90 |
| 7,045,069 B2 | 5/2006 | Ozeryansky |
| 2004/0094502 A1 * | 5/2004 | Boukobza ............ B65D 1/0284 215/375 |
| 2004/0094503 A1 * | 5/2004 | Ozeryansky ...... A61M 37/0015 216/2 |
| 2005/0000550 A1 | 1/2005 | Fick et al. |
| 2005/0015062 A1 | 1/2005 | Tamano |
| 2005/0017099 A1 * | 1/2005 | Batich ...................... B21C 5/00 239/589 |
| 2006/0247583 A1 * | 11/2006 | Klint .................... A61M 5/329 604/264 |
| 2008/0097330 A1 * | 4/2008 | King et al. ............... 604/164.02 |

FOREIGN PATENT DOCUMENTS

| | | |
|---|---|---|
| DE | 10 2007 022033 A1 | 11/2008 |
| EP | 1067591 A2 | 1/2001 |
| JP | 31-009364 | 11/1956 |
| JP | 61-021934 A | 1/1986 |
| WO | 93/17804 A1 | 9/1993 |
| WO | 02/076540 A1 | 10/2002 |
| WO | 2006/132602 A1 | 12/2006 |

OTHER PUBLICATIONS

ISO Standard No. 9626 Stainless Steel Needle Tubing for Manufacture of Medical Devices 2001.

Rao, P.N. & Kunzru, D., "Fabrication of Microchannels on Stainless Steel by Wet Chemical Etching," Journal of Micromechanics and Microengineering, Oct. 17, 2007.

* cited by examiner

METHOD FOR CHEMICAL ETCHING OF A NEEDLE CANNULA

CROSS-REFERENCE TO RELATED APPLICATIONS

This application is a 35 U.S.C. §371 national stage application of International Patent Application PCT/EP2010/063787 (published as WO 2011/033102), filed Sep. 20, 2010, which claimed priority of European Patent Application 09170828.9, filed Sep. 21, 2009, European Patent Application 09179188.9, filed Dec. 15, 2009, and European Patent Application 10156387.2, filed Mar. 12, 2010; this application further claims priority under 35 U.S.C. §119 of U.S. Provisional Application 61/245,435, filed Sep. 24, 2009.

THE TECHNICAL FIELD OF THE INVENTION

The invention relates to a method of manufacturing a needle cannula having improved flow properties and a needle cannula manufactured according to the method. The invention also relates to a tool for carrying out the method.

DESCRIPTION OF RELATED ART

Needle assemblies are commonly used to either inject substances into or extract substances out of human or animal bodies. Such needle assemblies are typically disposable and are discarded after only one use.

When producing needle assemblies a needle cannula which is typically drawn from stainless steel is attached to a hub generally moulded from a suitable polymer. The hub usually carries means for attaching the needle assembly to an injection device. The needle cannula is typically mounted to the hub such that a liquid communication patch can be established between the injection device, through the needle assembly and into the body of the user.

The needle cannula is normally made from a stainless-steel tube drawn through progressively smaller dies to make the needle the wanted diameter. The ratio between the outside diameter and the inside diameter is a result of the wall thickness of the stainless tube drawn and the diameter to which it is drawn. The specific dimensions used for a cylindrical needle cannula are given in ISO 9626.

Some drugs, such as insulin are self-administered, and the typical diabetes person will require subcutaneous injections of insulin several times during the course of the day. Recent studies have indicated that people who inject themselves experience less pain when using a thin needle i.e. a needle cannula having a little outside diameter. In order to reduce the discomfort of having to inject oneself several times a day, injection needles with a very thin needle cannula are very popular among people suffering from diabetes.

The outside diameter of a needle cannula is indicated by a "G" followed by a gauge number, which gauge number increases with thinner needles. At the present, the most commonly used injection needles among people suffering from diabetes are G30 or G31. Thus the outside diameter of a G 30 is according to ISO 9626 approximately 0.3 millimeters and of a G 31 approximately 0.25 millimeters.

U.S. Pat. No. 4,335,718 discloses a needle cannula which after it has been drawn is subjected to electro-chemical or chemical etching of the tip such that the outside diameter at the patient-end is decreased. The etching liquid also contacts the interior surface of the needle cannula thereby slightly increasing the internal diameter at the tip.

However, it is a problem for the etching liquid to penetrate in and out of the interior of the needle cannula due to the surface tension of the liquid bath, especially if the inside diameter is very small, which is the case for most needle cannulas today. If e.g. a G31 needle cannula is dipped in a liquid acid bath the liquid will not flow inside the lumen by itself under normal circumstances.

Electro polishing a needle cannula on the outside is also disclosed in WO 2002/076540.

US 2005/0015062 discloses an injection needle where the inside diameter of the needle cannula is expanded by cutting the narrow lumen with a drill.

A method of polishing a metallic tube on the inside is described in the article: "High Speed Slurry Flow Finishing of Inner Wall of Stainless Steel Capillary" by Toshiji Kurobe in International Journal of the Japan Society for Precision Engineering, Vol. 32, No. 1, in March 1998. By flushing a slurry containing grains through the entire lumen of a tube, the inside surface roughness can be lowered thereby enhancing the flow through the tube.

A different process for reducing the diameter of a metallic needle tube is disclosed in U.S. Pat. No. 3,326,786. In this process a liquid electrolyte solution is pumped into a pressure chamber holding a single metallic needle tube.

A process for removing a core of a needle cannula is disclosed in U.S. Pat. No. 3,192,084. In this process, the needle cannulas are submerged in a bath containing pressurized liquid acid and heated.

Fully developed laminar flows in pipes can be expressed by Pouseuilles formula. The flow of a liquid medicament through a thin metal needle cannula can in many aspects be assumed to also behave according to this formula. According to this formula, as explained in U.S. Pat. No. 5,951,528, it is preferred to have as large an inside diameter as possible and as short a length of the needle cannula as possible in order to maximise the flow through the needle cannula since the fourth ratio of the radius is divided with the length in the formula. When discussing a needle cannula tapered on the inside, the largest inside diameter must be on the longest part of the total length in order to increase the flow.

However, a large inside diameter, in order to increase the flow properties, and a small outside diameter, in order to minimize the pain perception, results in a needle cannula having a very thin wall thickness which makes the needle cannula easy breakable when bended.

DESCRIPTION OF THE INVENTION

It is an object of the present invention to provide a simple, cheap and reliable method for manufacturing a needle cannula with improved flow characteristic combining a small outside diameter with a satisfactory resistance against breakage when bended.

Further, it is an object to provide a method by which the interior material of a needle cannula can be chemically removed thereby increasing the flow through the needle cannula and especially a method by which material is removed from only a part of the axial length of the needle cannula thereby improving the flow through the needle cannula but maintaining the resistance against breakage.

According to the method described a metal etching liquid is transferred into a part of the interior lumen of a plurality of needle cannulas. By a part or limited part is here meant less than the full axial length of the needle cannula i.e. the liquid is transferred into only a part of the full length of the needle cannula as opposite to being washed all the through the lumen. The transfer of the metal etching liquid is preferably done continuously. By transferring or washing the liquid continuously is meant that the liquid is constantly shifted in and out of the lumen whereby various residual products are removed and fresh liquid is constantly applied to the lumen which speeds up the etching process. The metal etching liquid etches of the inside surface of the inside lumen thereby increasing the inside diameter of a part of the needle cannula. The diameter can be increased over a specific axial length of the needle cannula by controlling how far the metal etching liquid travels inside the lumen of the needle cannulas. Throughout the method a plurality of needle cannulas ("plurality" in the meaning of two or more needle cannulas) can be subjected to the method at the same time, the needle cannulas are preferably bundled together in bundles having an adequate size or mounted in a special tool.

In order to overcome the surface tension at the liquid surface and have the liquid flow into the opening of the lumen is has proven beneficial to pressurize the liquid before or when trans-ferring it into the lumen. When the metal etching liquid is subjected to pressure it penetrates into the lumen with no or very limited resistance.

One way of pressurizing the metal etching liquid could be to pump the liquid into the lumen as a pump would build up pressure in the liquid. An alternative to pumping the liquid into the needle cannula would be to subject the liquid to a centrifugal force such that a centrifugal force is built in the liquid. Once an adequate pressure is build up in the metal etching liquid, the needle cannulas and the liquid are moved relatively to each other. Once the needle cannula is moved into the metal etching liquid (or the liquid is moved into the needle cannula), the liquid will flow into the lumen of the needle cannulas. Due to the centrifugal force introduced into the liquid the surface tension when the needle cannula enters into the liquid will be eliminated and the liquid will flow into the lumen without any resistance. In addition, the liquid will flow into the lumen only the distance the needle cannula is moved into the liquid (or opposite). In this manner the length of the part of the lumen having its diameter increased can be easily controlled. Further, it has shown that higher rotational speed increases the forces acting on the etching liquid when the needle cannula is brought into and out of the liquid or opposite. If the inner diameter of the tubes is small then an increase in rotational speed should be considered to ensure that the liquid reaches a sufficient velocity when travelling inside the lumen.

A number of different metal etching liquids are usable for the process as described in "Fabrication of microchannels on stainless steel by wet chemical etching" by P. N. Rao and D. Kunzru published in Journal of Micromechanics and Microengineering 17 Oct. 2007. In order to increase the removal of material, polishing grains can be added to the metal etching liquid.

The outside surface of the needle cannulas are preferably coated with a coating that protects the outside surface from being etched in case the metal etching liquid contacts the outside surface of the needle cannulas. Such coatings could as an example be Ronascreen 1400 from Candor, Sweden or Miccro XP-2000 form Tolber, USA. The outside surface could alternatively be only partly coated such the outside surface is etched in controlled areas when the metal etching liquid contacts the outside surface. In this way side holes can be etched in the needle cannulas. The coating could in one example be applied as a rubber skin which could be easily removed after use.

The individual needle cannulas can be protected on their outside surface against the metal etching liquid by using cathodic protection. A sacrificial anode is placed in contact with the liquid and electrical connected to the individual needles. The electrical connection can be created through the supporting tool holding the needles. In order to have the outside surface of each needle cannula properly protected, the metal etching liquid most be able to come into contact with the surface of each needle cannula. The bundles of needle cannulas, if bundles are used, must then be made such that the liquid can flow between the individual needle cannulas. Preferably, the needle cannulas are placed in a supporting tool which both provides the needed distance between the individual needle cannulas as well as the electrical contact from each needle cannula and to the sacrificial anode. Since the ohmic drop is smaller on the outside surface than in the very narrow path forming the interior of the needle cannula, the current will travel on the outside surface, thereby protecting the outside surface from etching.

The cathodic protection system can also be of the type operating with an impressed current.

The needle cannulas can be physically moved in and out of the liquid by moving the needle cannulas perpendicular to the surface of the liquid or alternatively the liquid can be washed in and out of the needle cannulas. One way of doing this would be to provide the space inside the centrifuge with an overpressure forcing the liquid out of the needle cannulas dipped into the liquid. This process could be cycled such that the pressure in the centrifuge is continuously shifted from overpressure to atmospheric pressure.

The movement could also be any combination of a physical movement of the needle cannulas combined with a movement of the liquid acid.

The needle cannula obtained by the claimed method has an increased interior diameter over a limited part of its interior length.

The tool supporting the needle cannulas during the process preferably has a flexible part, e.g. made from rubber or latex, in which the needle cannulas are supported such that the rubber part prevents the metal etching liquid from contacting the area of the outside surface covered by the rubber part.

The needle cannulas can be released from the rubber part after being subjected to the metal etching liquid such that the needle cannulas can be easily removed.

The needle cannulas are preferably placed in the tool individually dislocated from each other in the axial direction such that the metal etching liquid travels the same distance into each single needle cannula. The axial distance between the individual needle cannulas being dependent on the diameter of the centrifuge used.

In one example the tool also provides electrical contact between all the individual needle cannulas supported by the tool.

Further the tool can be heated during the process preferably by heating a hollow space in the tool such that the individual metallic needle cannulas supported by the tool is also heated. Such heating of the individual needle cannulas helps control the effectiveness of the metal etching process being executed inside the lumen of the needle cannula as such metal etching liquids usually become more aggressive with rising temperatures.

Definitions:

According to ISO 9626, the dimensions for various gauges are as below:

| Guage Size | Designated Metric Size (mm) | Range of Outside Diameter (mm) | Min. inside Diameter (mm) |
| --- | --- | --- | --- |
| G33 | 0.2 | 0.203-0.216 | 0.089 |
| G32 | 0.23 | 0.229-0.241 | 0.089 |
| G31 | 0.25 | 0.245-0.267 | 0.114 |
| G30 | 0.3 | 0.298-0.320 | 0.133 |

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and Cpeptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

Further the term "injection needle" defines a piercing member adapted to penetrate the skin of a subject for the purpose of delivering or removing a liquid. The term "Needle Cannula" is used to describe the actual conduit performing the penetration of the skin during injection. A needle cannula is usually made from a metallic material such as stainless steel and connected to a hub to form an injection needle assembly. The "hub" being the part the needle cannula is mounted to and which carries the connecting means for connecting the needle cannula to an injection apparatus is usually moulded from a suitable thermoplastic material. The "needle assembly" is to be understood as the needle unit itself i.e. comprising a needle cannula mounted in a hub as supplied to the user.

"Cartridge" is the term used to describe the container containing the insulin. Cartridges are usually made from glass but could also be made from any suitable polymer e.g. by moulding or extrusion. A cartridge or ampoule is preferably sealed at one end by a pierceable membrane which can be pierced e.g. by an injection needle. The opposite end is closed by a plunger or piston made from rubber or a suitable polymer. The plunger or piston can be slidable moved inside the cartridge. The space between the pierceable membrane and the movable plunger holds the insulin which is pressed out as the plunger decreased the volume of the space holding the insulin. As an alternative to a cartridge, a flexible reservoir could be used.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the needle cannula penetrating the patient whereas the term "proximal end" is meant to refer to the opposite end of the needle cannula.

Figure 1:
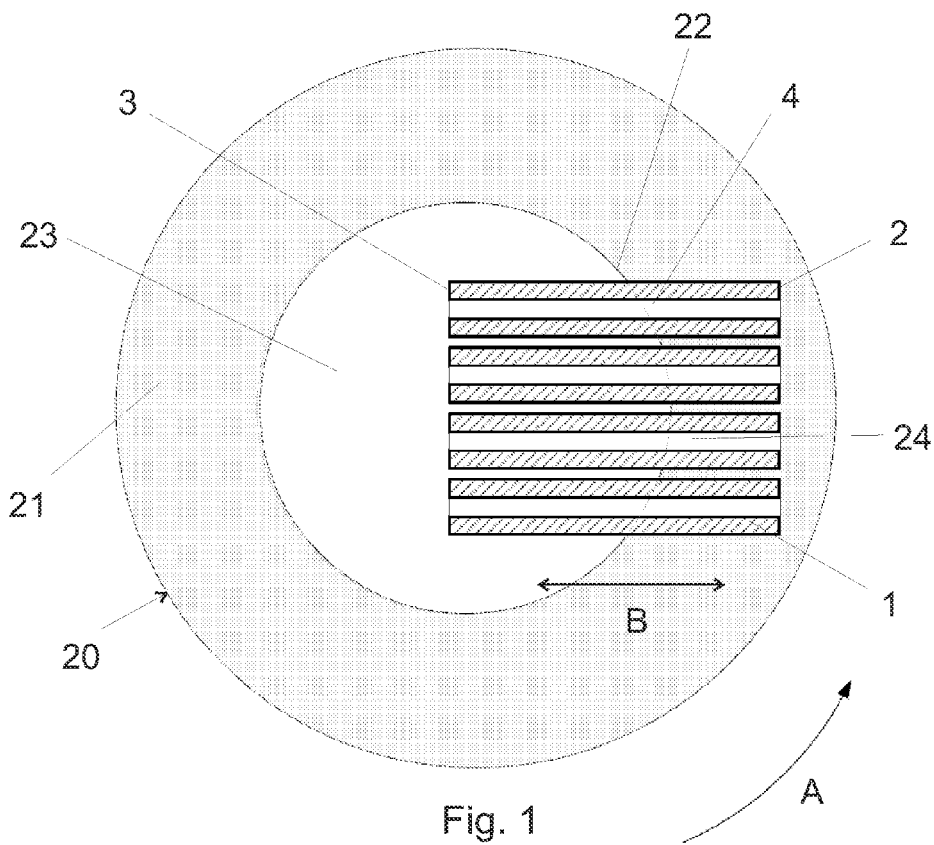
FIG. 1 show the method according to the invention
Figure 2:
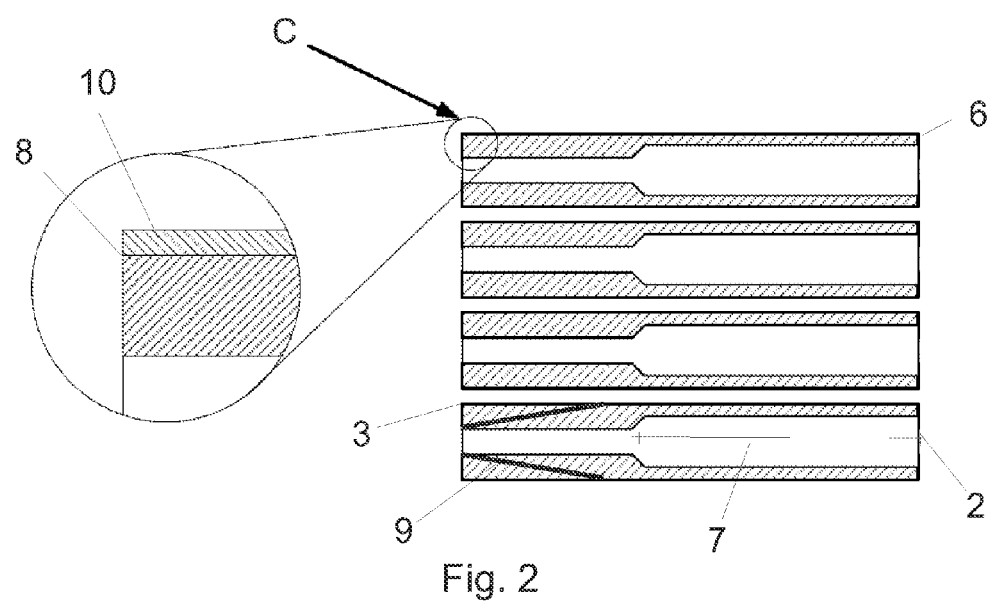
FIG. 2 show the needle cannulas resulting from the method

FIG. 1 discloses the process of manufacturing the needle cannulas 1 depictured in FIG. 2. A number of needle cannulas 1 having a back end 2 and a front end 3 and a lumen 4 there between are located inside a centrifuge 20 preferably in a not shown tool. A liquid 21 that is capable of etching a metallic surface is exposed to a centrifugal force by rotating the centrifuge 20 as indicated by the arrow A. During this rotation the liquid 21 will move towards the periphery of the centrifuge 20 leaving a centre area 23 with no liquid 21. The position of the surface 22 of the liquid will be a result of the rotation of the centrifuge 20. At the same time pressure will build up in the liquid 21. Once the centrifugal force has reached an adequate level the needle cannulas 1 are moved into the liquid 21 whereby the liquid 21 flows into the lumen 4 of the needle cannulas 1. The needle cannulas are preferably moved continuously in and out of the liquid 21 as indicated by the arrow B.

Figure 3:
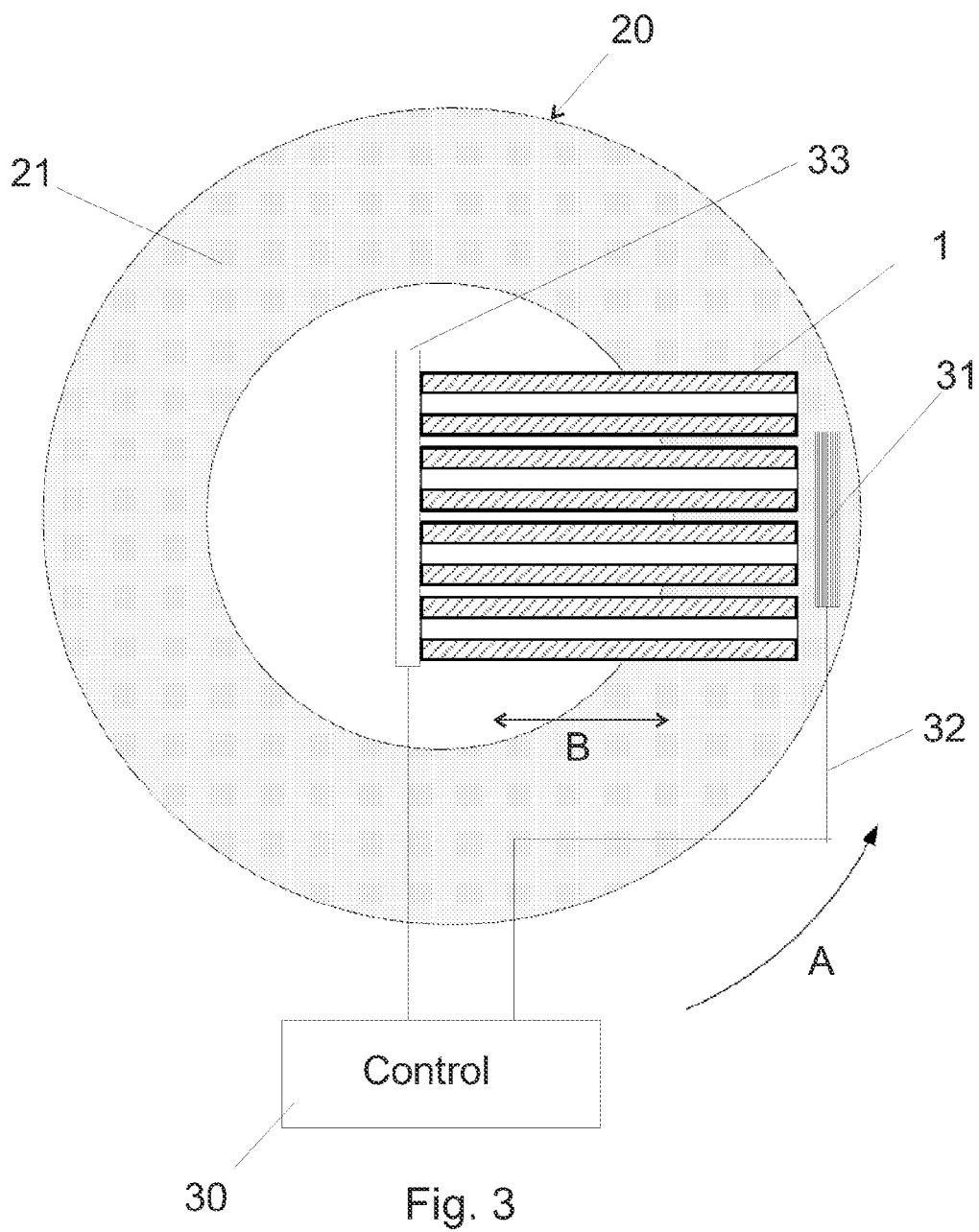
FIG. 3 show an alternative way of performing the method

Alternatively, the needle cannulas 1 can stay in the metal etching liquid 21 during the process and the liquid 21 can be moved in and out of the needle cannulas 1 by pressurizing the air contained in the centrifuge 20. If an overpressure is created in the centre area 23, the liquid 21 will be forced out of the lumen 4 of the needle cannulas 1 and when the overpressure is neutralized the liquid 21 will flow into the lumen 4 reaching the liquid surface 22 defined by the rotational force. In FIGS. 1 and 3 the needle cannulas 1 is depictured with an overpressure present in the centre area 23 such that the air contained in the centre area 23 is forced into the lumen 4 of each needle cannula 1 forcing the liquid 21 back towards the back end 2 of each needle cannula 21. The location of the surface 22 of the liquid 21 inside the lumen 4 when the overpressure is removed is illustrated with a dotted line 24 in FIG. 1.

The needle cannulas 1 resulting from the process is depictured in FIG. 2. The wall thickness 6 at the back end 2 has been reduced at a length or axial part 7 equal to the part of the needle cannula 1 that has been exposed to the metal etching liquid 21. The individual needle cannulas 1 are preferably supported dislocated form each other in the axial direction such that the length 7 in which the metallic material is removed is the same for all the needle cannulas 1 in a bundle. The dislocation depends upon the diameter of the surface 22 of the liquid 21. The front end 3 of each needle cannula 1 can further be subjected to electro-chemical etching as described in WO 2002/076540 thereby decreasing the outside diameter of the front end 3 by tapering 9 the outside surface at the distal end. The tapering 9 can be done by moving the front end 3 of the needle cannulas 1 into the metal etching liquid 21 in the centrifuge 20 or it can be done in a separate process. The tip diameter of a standard needle cannula 1 having an initial cylindrical outside can in this way be reduced to an outer diameter which is smaller than the inside diameter of the predominant part of the inside lumen 4.

In order to protect the outside surface 8 of the needle cannula 1 from the metal etching liquid 21, the outside surface 8 can be coated with a material 10 which are resistant to the metal etching liquid 21 used as depictured at C in FIG. 2. If wanted parts of the needle cannula 1 can remain un-coated during the process e.g. if side holes wants to be formed in the needle cannula 1.

As an alternative depictured in FIG. 3, the outside surface of the needle cannulas 1 can be protected by cathodic protection. A sacrificial anode 31 is placed in contact with the liquid 21 and brought into electrical contact with the outside surface of the needle cannulas 1 though a wire 32. The individual needle cannulas are electrical connected by a connector 33 which could form part of the supporting tool holding the needle cannulas 1. The sacrificial anode is made from a metal that is more active than the material forming the needle cannulas such that the anode is corroded first. A control unit 30 can be placed in the wire connection 32 in order to control the electrochemical process.

The control unit 30 can also impress a current on the cathodic protection system in which case the anode 31 can be of a material that are not easily dissolved in the etching liquid. The current impressed is then typically supplied by an external DC power unit.

Each needle cannula 1 is after being subjected to the described method grinded at both ends 2, 3 and mounted in a not shown hub and glued to the hub. The needle cannula 1 is preferably glued to the hub in a position where the wall thickness 6 is greatest thereby maximising the bending resistance. The back end 2 will in use enter into the cartridge of the injection device and the front end 3 enters into the skin of the patient.

Figure 4:
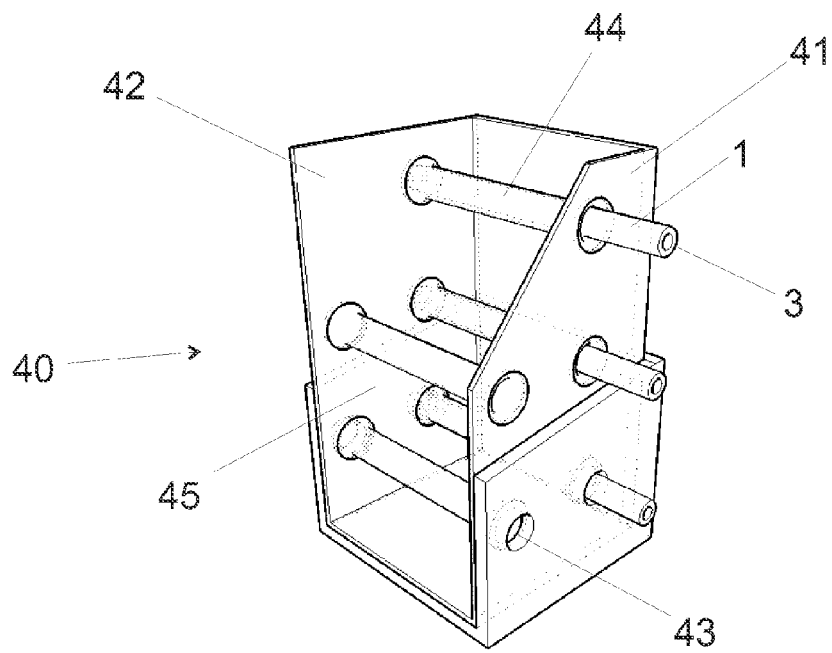
FIG. 4 show the tool used for the method

An example of a tool 40 usable for the method is disclosed in FIG. 4. The tool 40 preferably has a hollow space 45 with a first side 41 and a second side 42. These two sides 41, 42 are provided with a number of openings 43 which are connected by a flexible tube 44 e.g. made from latex. Needle cannulas 1 are inserted into the openings 41, 42 thereby penetrating through the flexible tubes 44. During the process, the hollow space 45 between the sides 41, 42 are pressurized such that the needle cannulas 1 are secured in their position having the front end 3 located outside the side 41 and the opposite back end 2 located outside the second side 42.

The air or liquid used for pressurising the hollow space is preferably warm such that the individual needle cannulas 1 are heated during the process in order to make the metal etching liquid 21 more aggressive and increase the effectiveness of the process. When moving the needle cannulas 1 in and out of the metal etching liquid 21 the part of the lumen 4 closest to the back end 2 is subjected to the metal etching liquid 21 for a longer time than the opposite end of the length or part 7 thereby given the inside lumen 4 a slightly conical appearance. This however can be compensated by heating the middle part of each needle cannula 1 thereby increasing the etching properties at the part on each needle cannula 1 being inside the hollow space 45 of the tool 40.

Figures 5A, 5B, 5C:
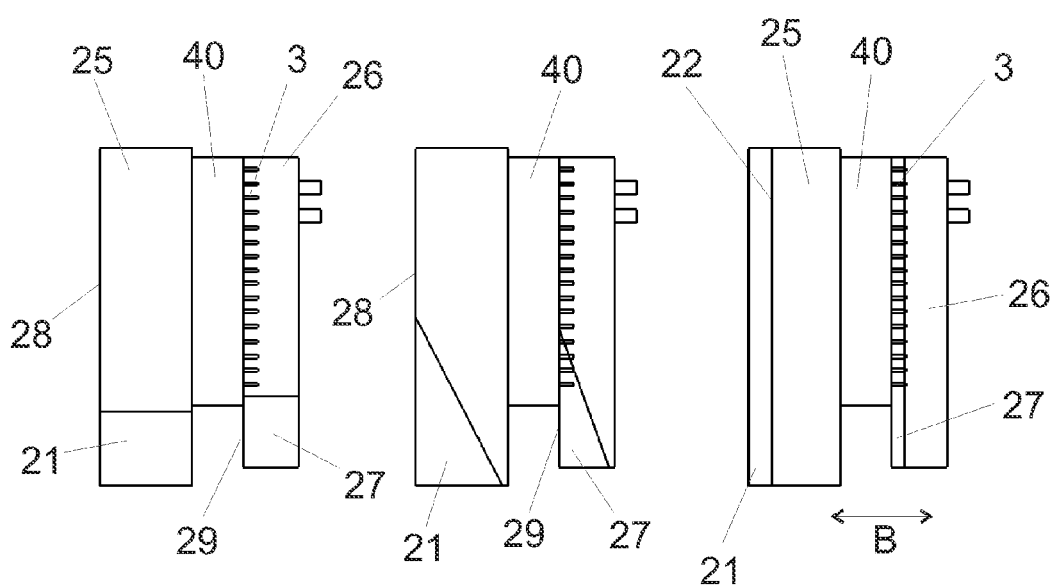
FIG. 5 A, B, C show a schematic overview of the process

FIG. 5 A, b and C discloses various steps of the process seen in a view tangential to the rotational direction of the centrifuge 20. In FIG. 5A the centrifuge has not started to rotate. The tool 40 is located between two semi open containers 25, 26 and placed inside the centrifuge 20. The first container 25 contains the metal etching liquid 21 and the second container 26 contains water 27 (or a similar liquid).

The front end 3 of the needles cannulas 1 are inserted into the second container 26.

In FIG. 5B the centrifuge 20 has started to rotate and the metal etching liquid 21 starts climbing up the wall 28 of the first container 25 and the water 27 starts to climb up the wall 29 of the second container 26.

In FIG. 5C the centrifuge 20 has reached its process speed and the metal etching liquid 21 is pressed towards the wall 28 thereby obtaining a vertical liquid surface 22 inside the first container. In the second container the water 27 is pressed against the wall 29 also reaching a vertical stage.

With the centrifuge 20 is rotating with a suitable angular velocity the tool 40 holding the needle cannulas 1 can be moved in and out (B) of the first container 25 such that the back end 2 penetrates through the liquid surface 22 thereby allowing the metal etching liquid 21 to enter a part 7 of each needle cannula 1. The second container 26 are moved simultaneously with the tool 40 such that the front end 3 of the needle cannulas 1 are constantly submerged into the water 27 inside the second container 26 thereby protecting the frontal part of the inside lumen 4 form splashes of the metal etching liquid 21.

EXAMPLE

Stainless G31 steel tubes having the following characteristic were covered on their outer surfaces with melted wax:
Length: 100 mm,
Outer diameter: 0.26 mm,
Inner diameter: 0.15 mm,
Steel type: AISI 304L
Wax type: Freeman Flakes, Premium Injection Wax with a melting temperature of 60° C.

A coherent bundle of 100 waxed tubes were then formed by application of heat and force. The bundle was cut into shorter bundles having a length of 18 mm.

A short bundle was placed in a centrifuge and subjected to 600 RPM. This resulted in a centripetal acceleration of approximately 100 times the gravitational acceleration (100G).

The bundle was during centrifugation dipped repeatedly in an etching solution having a composition of: 10 wt % $FeCl_3$, 10 wt % HCL and 5 wt % $HNO_3$.

The solution was maintained at 25° C. The bundle was moved into the etching solution such that it travelled 15 mm inside the tubes during a dipping cycle.

A cycle consisted of 1 sec. for moving the bundle into position in the etching solution, followed by 5 sec. resting in the etching solution and finally 1 sec. for bringing the bundle out of the etching solution. The described cycle was repeated 400 times.

The inner diameter was thus increased from 0.15 mm to 0.18 mm on the 15 mm length being subjected to the etching solution resulting in an increase in the flow rate of approximately 100% for a given pressure drop of 1 bar.

Some preferred embodiments have been shown in the foregoing, but it should be stressed that the invention is not limited to these, but may be embodied in other ways within the subject matter defined in the following claims.

The invention claimed is:

1. A method of manufacturing needle cannulas comprising:
   providing a plurality of metallic needle cannulas (1) having a back end (2) and a front end (3) and an oblong inside lumen (4) there between,
   providing a protection on at least a part of the outside surface (8) of at least one of the plurality of needle cannulas (1),
   providing a pressurized metal etching liquid (21),
   the needle cannula comprises a part (7) having a length less than the full axial length of the needle, and a remaining part having a length corresponding to the full axial length minus the length of the part (7),
   transferring the pressurized metal etching liquid (21) into a part (7) of the oblong inside lumen (4) of the metallic needle cannula (1), wherein the protected part of the outside surface (8) is commensurate with the part (7), thereby the etching increases a diameter of the part (7) of the inside lumen (4) without decreasing the outer diameter of the needle cannulas (1) in the areas where the protection of the outside surface of the at least one of the plurality of needle cannulas is provided, and thereby obtaining at least one needle cannula having a reduced wall thickness at the back end (2) at a length corresponding to the axial part (7), and an unchanged wall thickness at the front end (3) corresponding to the remaining part.

2. A method of manufacturing needle cannulas according to claim 1 further comprising:
   exposing the metal etching liquid (21) to a centrifugal force, thereby building up pressure in the metal etching liquid (21).

3. A method of manufacturing needle cannulas according to claim 1, where the diameter of the part (7) of the inside lumen (4) is increased by controlling how far the metal etching liquid (21) travels inside the lumen (4) of the needle cannula (1).

4. A method of manufacturing needle cannulas according to claim 1, wherein the protection on at least a part of the outside surface of at least one of the plurality of needle cannulas comprises a coating, or a sacrificial anode placed in contact with the etching liquid.

5. A method of manufacturing needle cannulas according to claim 1 further comprising:
   pumping the metal etching liquid (21) into the part (7) of the inside lumen (4) of the metallic needle cannulas (1) thereby building up pressure in the metal etching liquid (21).

6. A method of manufacturing needle cannulas according to claim 5 further comprising:
   cathodic protecting the individual needle cannulas (1) by providing a sacrificial anode (31) in contact with the metal etching liquid (21) and in electrical contact with each individual needle cannula (1).

7. A tool (40) for supporting the plurality of needle cannulas (1) when subjected to the method of claim 2, the tool (40) comprising a plurality of flexible parts (44) which each seals an area of the outside surface of each needle cannula (1) from being in contact with the metal etching liquid (21) during the execution of the method.

8. A method of manufacturing needle cannulas according to claim 7 further comprising:
   moving the metallic needle cannulas (1) and the metal etching liquid (21) relatively to each other such that the etching liquid flows into a part (7) of the inside lumen (4).

9. A method of manufacturing needle cannulas according to claim 8 wherein the metallic needle cannulas (1) are moved relatively to metal etching liquid (21).

10. A method of manufacturing needle cannulas according to claim 8 wherein the metal etching liquid (21) is moved relatively to the metallic needle cannulas (1).

* * * * *